United States Patent [19]

Sekizawa et al.

[11] Patent Number: 4,849,560
[45] Date of Patent: Jul. 18, 1989

[54] PROCESS FOR PREPARATION OF HALOGENATED BENZENE DERIVATIVES

[75] Inventors: Kazuhiko Sekizawa; Takanori Miyake, both of Shinnanyo; Toshio Hironaka; Yukihiro Tsutsumi, both of Tokuyama, all of Japan

[73] Assignee: Toyo Soda Manufacturing Co., Ltd., Shinnanyo, Japan

[21] Appl. No.: 235,839

[22] Filed: Aug. 24, 1988

Related U.S. Application Data

[63] Continuation of Ser. No. 83,006, Aug. 6, 1987, abandoned, which is a continuation of Ser. No. 829,905, Feb. 8, 1986, abandoned.

[30] Foreign Application Priority Data

Feb. 18, 1985 [JP] Japan ................................... 60-28466

[51] Int. Cl.$^4$ .............................................. C07C 17/12
[52] U.S. Cl. .................................... 570/208; 570/206; 570/207
[58] Field of Search ................ 570/197, 206, 208, 207

[56] References Cited

U.S. PATENT DOCUMENTS

| | | | |
|---|---|---|---|
| 2,473,990 | 2/1946 | Darragh | 570/208 |
| 2,956,084 | 10/1960 | Eng et al. | 570/197 |

FOREIGN PATENT DOCUMENTS

| | | | |
|---|---|---|---|
| 118851 | 9/1974 | European Pat. Off. | 570/208 |
| 112722 | 7/1984 | European Pat. Off. | 570/208 |
| 171265 | 2/1986 | European Pat. Off. | 570/206 |
| 77631 | 5/1982 | Japan | 570/206 |
| 144722 | 8/1984 | Japan | 570/197 |
| 650985 | 3/1979 | U.S.S.R. | 570/208 |

OTHER PUBLICATIONS

Wortel et al., "Jour. of Catalysis" Volume 60, pp. 110–120, (1979).

*Primary Examiner*—Werren B. Lone
*Attorney, Agent, or Firm*—Oblon, Spivak, McClelland, Maier & Neustadt

[57] ABSTRACT p-Substituted halogenated benzene derivatives are prepared at a high selectivity by halogenating benzene and/or benzene derivatives by using as a catalyst a zeolite modified with a metal salt.

12 Claims, No Drawings

PROCESS FOR PREPARATION OF HALOGENATED BENZENE DERIVATIVES

This application is a continuation of application of Ser. No. 06/629,905 filed Feb. 18, 1986, now abandoned which is a continuation of application number 07/083,006, filed Aug. 6, 1987, now abandoned.

BACKGROUND OF THE INVENTION

(1) Field of the Invention

The present invention relates to a process for preparing a halogenated benzene derivative by halogenating benzene and/or a benzene derivative in the presence of a zeolite as the catalyst. More particularly, the present invention relates to a process for selectively preparing a p-substituted halogenated benzene derivative by halogenating benzene and/or a benzene derivative, which is characterized in that a zeolite modified with a metal salt is used as a catalyst.

(2) Description of the Related Art

Halogenated benzene derivatives, especially di-substituted halogenated benzene derivatives, are industrially important as intermediate compounds for the production of various compounds. A di-substituted halogenated benzene derivative includes three isomers, that is, ortho-, meta-, and para-isomers, and p-substituted halogenated benzene derivatives are especially important for the production of various organic compounds. Para-dichlorobenzene (hereinafter referred to as PDCB), which is a p-substituted halogenated benzene derivative, is used as a starting material in medicines and agricultural chemicals and is directly used as an insecticide or deodorizer, and hence, this compound is very valuable from an industrial viewpoint.

At the present, dichlorobenzene (hereinafter referred to as DCB) is industrially prepared by blowing chlorine into benzene or monochlorobenzene (hereinafter referred to as MCB) in the presence of a Lewis acid catalyst such as ferric chloride or aluminum chloride to effect chlorination. DCB prepared according to this process comprises 30 to 40% of the ortho-isomer, about 5% of the meta-isomer, and 60 to 70% of the para-isomer, and it is difficult to make any great change in this formation ratio in these three isomers.

Various research works have been carried out with a view to improving the selectivity to the paraisomer in the above-mentioned process. For example, there can be mentioned a method using a zeolite as the catalyst. More specifically, Journal of Catalysis, 60, pages 110–120 (1979) teaches that, if various ion-exchanged X-type or Y-type zeolites are used as the catalyst for the liquid phase bromination of a halogenated benzene, the para-isomer can be formed at a much higher selectivity than the selectivity attained in the conventional method using a Lewis acid as the catalyst. Furthermore, Japanese Unexamined Patent Publication No. 59-163,329 teaches that, if zeolite L is used for the liquid phase nuclear halogenation of benzenes, p-dihalogenated benznes can be prepared at a high selectivity. In connection with the gas phase halogenation, it is known that PDCB is obtained at a higher selectivity than the selectivity attainable in the conventional process if MCB is chlorinated by using a catalyst consisting of a zeolite having a pore size of 5 to 13 angstrom, such as molecular sieve 5A, 10X or 13X or zeolite HY (see Japanese Unexamined Patent Publication No. 57-77,631).

It is now considered that the demand for p-substituted halogenated benzene derivatives among di-substituted halogenated benzene derivatives will vigorously increase in the future. Accordingly, it is very important from the industrial viewpoint to selectively produce a p-substituted halogenated benzene while controlling the ratios of o-substituted and m-substituted halogenated benzene derivatives, formed as by-products, to levels as low as possible.

As pointed out above, in the selective production of p-substituted halogenated benzene derivatives by the halogenation of benzene or benzene derivatives, methods using zeolites as the catalyst are effective over the conventional methods. However, all of the known methods using zeolites are still insufficient from the industrial viewpoint because the selectivity to di-substituted halogenated benzene derivatives is not satisfactory.

SUMMARY OF THE INVENTION

In view of the foregoing, it is an object of the present invention to provide a process for the preparation of p-substituted halogenated benzene derivatives wherein the p-substituted halogenated benzene derivative can be prepared at an enhanced activity and a higher selectivity than the selctivity attainable in the conventional process.

In accordance with the present invention, there is provided a process for the preparation of p-substituted halogenated benzene derivatives, which comprises halogenating benzene and/or a benzene derivative, wherein a zeolite modified with a metal salt is used as a catalyst for the halogenation.

DESCRIPTION OF THE PREFERRED EMBODIMENTS

In the process of the present invention, a zeolite is used as the catalyst, and the zeolite is generally known as a crystalline metallosilicate. A crystalline aluminosilicate, a most popular zeolite, consists of tetrahedrons of $SiO_4$ and $AlO_4$, and many kinds are known differing in the manner of bonding of the tetrahedrons. Zeolites include natural and synthetic products, and in the present invention, both natural and synthetic products can be used as the starting material of the catalyst. However, a synthetic zeolite having a low impurity content and a high crystallinity is generally preferred. Synthetic zeolites prepared by known methods can be used and the preparation process is not particularly critical. As preferred examples of the zeolite, there can be mentioned zeolite Y, zeolite L, zeolite X, gmelinite, offretite/erionite type zeolite, mordenite, and zeolite ZSM-5. From the industrial viewpoint, zeolite Y and zeolite L are especially preferred. The zeolite ordinarily contains a proton and/or a cation so that the charge possessed by the zeolite per se is neutralized. The kind of the cation is not particularly critical in the zeolite used in the present invention. For example, an as-prepared zeolite may be used without a treatment such as ion exchange, or a zeolite formed by subjecting an as-synthesized zeolite to such a treatment may be used.

In the present invention, a zeolite modified with a metal salt is used as the catalyst. In the present invention, "modification of a zeolite with a metal salt" means that a zeolite is placed in intimate contact with a metal salt. Accordingly, the state where the metal salt is present on the outer surfaces of zeolite particles and/or in pores of the zeolite is included in the definition of "modification of a zeolite with a metal salt" referred to in the present invention. Moreover, the state in which a part of the metal salt is occluded in the skeleton structure of the zeolite is within the scope of the present invention. The method for the modification of the zeolite with the metal salt is not particularly critical in the present invention. For example, ordinary impregnation, mixing, and kneading methods may be adopted.

An ordinary impregnation method comprising dissolving the metal salt in an appropriate solvent and impregnating the zeolite with the solution is preferred, because the method is simple and not only outer surfaces of the zeolite particles but also interiors of the pores of the zeolite can be modified uniformly and densely.

The kind of metal salt is not particularly critical, in so far as the metal salt is not reactive with a halogenating agent during the halogenation reaction. The modified catalyst may be directly used. If a metal salt which reacts with a halogenating agent during the halogenation reaction is used, the modified zeolite may be used as the catalyst after the preliminary treatment with the halogenating agent. A halide, nitrate, carbonate or sulfate of an alkali metal, alkaline earth metal or rare earth metal can be used as the metal salt. For example, there can be mentioned chlorides such as lithium chloride, sodium chloride, potassium chloride, rubidium chloride, cesium chloride, magnesium chloride, calcium chloride, strontium chloride, barium chloride, lanthanum chloride, cerium chloride, praseodymium chloride, neodium chloride, and thiorium chloride; nitrates such as lithium nitrate, sodium nitrate, potassium nitrate, rubidium nitrate, cesium nitrate, magnesium nitrate, calcium nitrate, strontium nitrate, barium nitrate, lanthanum nitrate, cerium nitrate, neodium nitrate, and thorium nitrate; carbonates such as lithium carbonate, sodium carbonate, potassium carbonate, rubidium carbonate, cesium carbonate, magnesium carbonate, calcium carbonate, strontium carbonate, barium carbonate, and lanthanum carbonate; and sulfates such as lithium sulfate, sodium sulfate, potassium sulfate, rubidium sulfate, cesium sulfate, magnesium sulfate, calcium sulfate, strontium sulfate, barium sulfate, and lanthanum sulfate. Of these, sodium chloride, potassium chloride, rubidium chloride, cesium chloride, magnesium chloride, calcium chloride, strontium chloride, barium chloride, lanthanum chloride, sodium nitrate, potassium nitrate, rubidium nitrate, cesium nitrate, magnesium nitrate, calcium nitrate, strontium nitrate, barium nitrate, lanthanum nitrate, sodium carbonate, potassium carbonate, magnesium carbonate, calcium carbonate, strontium carbonate, barium carbonate, lanthanum carbonate, sodium sulfate, potassium sulfate, magnesium sulfate, calcium sulfate, strontium sulfate, barium sulfate, and lanthanum sulfate are preferred. Sodium chloride, potassium chloride, strontium chloride, barium chloride, sodium carbonate, potassium carbonate, strontium carbonate, barium carbonate, sodium sulfate, potassium sulfate, strontium sulfate, and barium sulfate are especially preferred. Naturally, the preferred amount of the metal salt should be changed according to the kind of zeolite to be used, but it is generally preferred that the amount of the metal salt to be used for the modification be 0.1 to 90% by weight, especially 10 to 80% by weight, based on the catalyst. If the amount of the metal salt is too small, a sufficient effect cannot be obtained, and if the amount of the metal salt is too large, the activity of the catalyst is reduced.

A solvent capable of dissolving a predetermined amount of the metal salt therein may be used as the solvent for performing the modification according to the impregnation method, and water is practically preferred. The amount of the solvent is not particularly critical, in so far as the solution of the metal salt uniformly permeates the entire zeolite. Removal of the solvent is accomplished by evaporating the solvent under atmospheric pressure or reduced pressure while sufficiently stirring the slurry containing the zeolite and metal salt. In the case of the modification by the impregnation method, it is considered that in a certain combination of the zeolite and metal salt, ion exchange is caused between the cation present in the zeolite skeleton and the metal cation of the metal salt used for the modification. However, this ion exchange is permissible in the present invention because, in consequence, the metal salt formed by the ion exchange modifies the zeolite. The obtained metal salt-modified zeolite is dried at 80° to 150° C. for 1 to 24 hours and is used as the catalyst directly or after it is calcined for 10 minutes to 24 hours in a stream of air or an inert gas such as nitrogen or helium. Obviously, the calcination temperature should be lower than a temperature at which breakage of the structure of the metal salt-modified zeolite will occur. It is preferred that the calcination temperature be 200 to 900° C., especially 300° to 850° C. Some of the above-mentioned metal salts are thermally decomposed at this calcination step, but this thermal decomposition is permissible because the decomposition product is very stable against the halogenating agent. The operation of modifying the zeolite with the metal salt, an embodiment of which has been described, may be carried out so that the desired amount of the metal salt is included in the zeolite by one operation. Alternatively, the operation of impregnation and drying may be repeated. Moreover, after the metal salt-modified zeolite has been calcined at a desired temperature, the operation of impregnation, drying, and calcination may be repeated.

A modifying effect can be attained by a physical method comprising mixing dried zeolite and metal salt in a ceramic mortar of the like. However, it is preferred that physical mixing be carried out in the state where the zeolite per se contains water in an amount of at least 0.1% by weight, especially at least 0.5% by weight, based on the zeolite. The amount of water referred to herein is the amount measured as the weight loss by removal of water by using a thermobalance when the temperature is elevated from room temperature to 500° C. Furthermore, the metal salt-modified zeolite catalyst may be prepared according to a customary kneading method. The thus-prepared modified zeolite is used as the catalyst after drying and calcination have been conducted in the same manner as in the ordinary impregnation method.

In the present invention, the term "benzene derivative" means a compound in which a hydrogen atom of benzene is substituted by a substituent such as a halogen atom or an alkyl group having 1 to 10 carbon atoms, such as mono-halogenated benzene or monoalkylbenzene. alkylbenzene. A preferable mono-alkylbenzene has 1 to 4 carbon atoms in the alkyl group. The benzene derivative includes, for example, MCB, monobromobenzene, monofluorobenzene, monoiodobenzene, toluene, and ethylbenzene. An elementary halogen element may be used as the halogenating agent. For example, there may be used chlorine, bromine, and iodine.

In the present invention, the reaction apparatus, reaction procedure, and reaction condition are not particularly critical in so far as benzene and/or a benzene derivative is efficiently placed in contact with the halogenating agent on the catalyst. The halogenation reaction may be carried out in either the gas phase or the liquid phase, but the liquid phase reaction is preferred. Any of a batchwise reactor, a semi-batchwise reactor, and a continuous reactor may be used as the reaction vessel. The catalyst may be used in the form of a fixed bed or fluidized bed. A solvent inactive to the halogenation reaction may be used as a diluent. When the solvent is used, it is preferred that the concentration of benzene and/or a benzene derivative be 5 to 100% by weight, especially 10 to 100% by weight. If the concentration is lower than 5% by weight, the contact between the catalyst and starting material becomes insufficient and the reaction efficiency is reduced. If the halogenating agent is continuously supplied, a gas inactive to the reaction, such as nitrogen or helium, may be used as a diluent. In this case, it is preferred that the concentration of the halogenating agent be 5 to 100% by volume, especially 10 to 100% by volume. Furthermore, when the continuous reactor is used as the reactor, it is preferred that the molar ratio of the halogenating agent to benzene and/or a benzene derivative be from 0.01 to 5, especially from 0.1 to 2.0.

When a batchwise or semi-batchwise reactor is used, the catalyst is used usually in the state suspended in the reaction liquid, and the amount of the catalyst per unit volume of the reaction liquid is preferably 0.0001 to 1 kg/l, especially preferably 0.001 to 0.1 kg/l. If the amount of the catalyst is smaller than 0.0001 to 1 kg/l, the load on the catalyst is too large and a sufficient conversion cannot be obtained. If the amount of the catalyst exceeds 1 kg/l, the effect is not proportionally increased. When a continuous reactor is used, the amount of the catalyst varies greatly depending upon the manner in which the catalyst is used. In the case where the halogenating agent is continuously supplied, the feed rate of the halogenating agent (the feed rate of the halogenating agent per unit volume of the reaction liquid) is preferably 1 to 1000 l/l·hr and especially preferably 5 to 500 l/l·hr. If the feed rate of the halogenating agent is lower than 1, a sufficient rate of reaction cannot be obtained, and if the feed rate of the halogenating agent exceeds 1,000, the rate of reaction is controlled by diffusion and a substantial effect cannot be attained by increase of the feed rate of the halogenating agent.

The reaction temperature and reaction pressure are not particularly critical, in so far as benzene and/or a benzene derivative is in the liquid phase. In the case where the reaction temperature is higher than the boiling point of benzene and/or a benzene derivative, the halogenation reaction can be carried out in the liquid phase if the pressure is elevated. It is preferred that the reaction temperature be 0° to 400° C., more preferably 20° to 300° C. The optimum temperature is 20 to 150° C. If the reaction temperature is lower than 0° C., a sufficient reaction speed cannot be obtained, and if the reaction temperature is higher than 400° C., the selectivity to the intended p-substituted halogenated benzene derivative is reduced.

According to the present invention, a p-substituted halogenated benzene derivative having a very high industrial value can be prepared in a much higher yield than in the known processes.

The present invention will now be described in detail with reference to the following examples that by no means limits the scope of the invention. Note, in the following examples and comparative examples, the conversion and selectivity were calculated according to the following formulae.

$$\text{Conversion} = \frac{BS - BU}{BS} \times 100$$

wherein BS is the amount (millimoles) of charged or supplied benzene or benzene derivative, and BU is the amount (millimoles) of unreacted benzene or benzene derivative. Selectivity=(AP/AT)×100 wherein AP is the amount (millimoles) of the intended compound formed and AT is the amount (millimoles) of all the compounds formed.

In the examples given hereinafter, zeolites and catalysts are indicated in the following manner. For example, in the case of "Na-Y-30 wt. % NaCl", Na indicates the cation present in the zeolite skeleton, Y indicates the type of the zeolite, and 30 wt. % NaCl indicates the kind and amount of the metal salt used for the modification. In the case of "Na-Y", Na indicates the cation present in the zeolite skeleton and Y indicates the type of the zeolite.

EXAMPLE 1

A ceramic beaker having a capacity of 1 liter was charged with 4.29 g of sodium chloride, and the sodium chloride was dissolved in 150 ml of distilled water. The solution was maintained at 95° C. by using a warm bath, and 10 g of Na-Y was added to the solution with sufficient stirring by a glass stirring vane. Evaporation to dryness was effected on the warm bath until water was completely removed. The solid was dried for 15 hours in a drier maintained at 130° C. and calcined at 540° C. for 3 hours under air circulation to obtain a zeolite catalyst of Na-Y-30 wt. % NaCl.

The chlorination reaction of MCB was carried out by using this catalyst in an ordinary semi-batchwise reactor. More specifically, 40 g of MCB and 1.428 g of the zeolite catalyst (containing 1 g of the zeolite) were charged in a Pyrex reaction vessel having a capacity of 126 ml (having an inner diameter of 40 mm and a height of 100 mm), and chlorine gas (containing an equal amount of nitrogen gas) was blown at a rate of 80 millimoles per hour with sufficient stirring by a magnetic stirrer. The reaction temperature was adjusted to 100° C. The product obtained when 3 hours had passed from the start of the blowing of chlorine gas was analyzed by gas chromatography. The obtained results are shown in Table 1.

EXAMPLE 2 THROUGH 7

The chlorination reaction of MCB was carried out in the same manner as described in Example 1 except that the amount of sodium chloride content was 10, 20, 40, 50, 60 or 80% by weight. The obtaining results are shown in Table 1. It will be readily understood that, if sodium chloride is incorporated into the zeolite, the para-selectivity is improved by about 7%.

TABLE 1

| | Catalyst | Conversion (%) of MCB | Selectivity (%) to PDCB |
|---|---|---|---|
| Example 1 | Na—Y—30 wt. % NaCl | 67.5 | 85.1 |

TABLE 1-continued

| | Catalyst | Conversion (%) of MCB | Selectivity (%) to PDCB |
|---|---|---|---|
| Example 2 | Na—Y—10 wt. % NaCl | 68.9 | 82.7 |
| Example 3 | Na—Y—20 wt. % NaCl | 68.5 | 83.5 |
| Example 4 | Na—Y—40 wt. % NaCl | 69.0 | 84.8 |
| Example 5 | Na—Y—50 wt. % NaCl | 69.7 | 85.1 |
| Example 6 | Na—Y—60 wt. % Na Cl | 70.2 | 85.4 |
| Example 7 | Na—Y—80 wt. % NaCl | 69.8. | 84.6 |

EXAMPLES 8 THROUGH 12

A catalyst was prepared in the same manner as described in Example 1 except that potassium chloride, cesium chloride, calcium chloride, strontium chloride or barium chloride was used instead of sodium chloride, and by using this catalyst, the chlorination reaction of MCB was carried out in the same manner as described in Example 1. The obtained results are shown in Table 2.

COMPARATIVE EXAMPLE 2

A 2N aqueous solution of potassium chloride containing a potassium (K) ion in an amount 20 times the amount of a sodiuim (Na) ion contained in 10 g of Na-Y was prepared, and the solution was maintained at 90° C. by using a mantle heater. Then, 10 g of Na-Y was added to the solution and the mixture was sufficiently stirred for 5 hours by a glass stirring vane. The obtained slurry was filtered and the solid was washed with 10 l of distilled water. The washed solid was dried for 15 hours in a drier maintained at 130° C. and calcined at 540° C. for 3 hours under air circulation. By using 10 g of the thus-obtained K-Y, the chlorination reaction of MCB was carried out in the same manner as described in Example 1. The obtained results are shown in Table 2.

COMPARATIVE EXAMPLE 3 THROUGH 6

Cs-Y, Ca-Y, Sr-Y and Ba-Y were prepared in the same manner as described in Comparative Example 2, and by using these catalysts, the chlorination reaction of MCB was carried out in the same manner as described in Example 1. The obtained results are shown in Table 2.

EXAMPLE 13

The Sr-Y prepared in Comparative Example 5 was modified with 30% by weight of strontium chloride in the same manner as described in Example 1. By using the thus-obtained catalyst, the chlorination reaction of MCB was carried out in the same manner as described in Example 1. The obtained results are shown in Table 2.

TABLE 2

| | Catalyst | Conversion (%) of MCB | Selectivity (%) to PDCB |
|---|---|---|---|
| Comparative Example 2 | K—Y | 57.8 | 67.2 |
| Example 8 | Na—Y—30 wt. % KCl | 56.5 | 71.2 |
| Comparative Example 3 | Cs—Y | 22.4 | 70.3 |
| Example 9 | Na—Y—30 wt. % CsCl | 61.6 | 75.3 |
| Comparative Example 4 | Ca—Y | 63.5 | 69.9 |
| Example 10 | Na—Y—30 wt. % CaCl$_2$ | 69.2 | 72.2 |
| Comparative Example 5 | Sr—Y | 64.9 | 72.8 |
| Example 11 | Na—Y—30 wt. % SrCl$_2$ | 71.6 | 80.5 |
| Example 13 | Sr—Y—30 wt. % SrCl$_2$ | 66.1 | 76.9 |
| Comparative Example 6 | Ba—Y | 67.8 | 75.1 |
| Example 12 | Na—Y—30 wt. % BaCl$_2$ | 68.1 | 80.5 |

EXAMPLES 14 AND 15

Catalysts were prepared in the same manner as described in Example 1 except that sodium carbonate or sodium sulfate was used instead of sodium chloride. By using these catalysts, the chlorination reaction was carried out in the same manner as described in Example 1. The obtained results are shown in Table 3.

TABLE 3

| | Catalyst | Conversion (%) of MCB | Selectivity (%) to PDCB |
|---|---|---|---|
| Example 14 | Na—Y—30 wt. % Na$_2$CO$_3$ | 64.8 | 80.7 |
| Example 15 | Na—Y—30 wt. % Na$_2$SO$_4$ | 68.5 | 83.1 |

EXAMPLE 16

A continuous reaction vessel having an inner diameter of 17 mm and an inner capacity of 17.1 ml, and equipped with a catalyst separator, was charged with 16 g of MCB, and 1.67 g of the Na-Y-40 wt. % NaCl catalyst prepared in Example 4 was added. Then, MCB and chlorine were fed into the reaction vessel at rates of 133 millimoles per hour and 95.8 millimoles per hour, respectively. Thus, the continuous chlorination reaction of MCB was carried out at 100° C. The product overflowing from the reaction vessel was analyzed by gas chromatography. It was found that the conversion of MCB was 68.9%, the selectivity to DCB higher than 99%, nd the selectivity to PDCB was 84.6%. The composition of the product was not changed with the lapse of time. Thus, it was confirmed that if a zeolite catalyst having sodium chloride included therein is used, a p-substituted halogenated benzene derivative can be prepared in a high yield even by the continuous reaction.

EXAMPLE 17

A ceramic beaker having a capacity of 1 litter was charged with 1.11 g of potassium chloride, and the potassium chloride was dissolved in 150 ml of distilled water. The solution was maintained at 95° C. by using a warm bath, and 10 g of K-L was added to the solution with sufficient stirring by a glass stirring vane. Evaporation to dryness was conducted on the warm bath until water was completely removed. The solid was dried for 15 hours in a drier maintained at 130° C. and calcined at 540° C. for 3 hours under the circulation of air to obtain a catalyst of K-L-10 wt. % KCl zeolite. By using 1.11 g of the thus-obtained catalyst, the chlorination reaction of MCB was carried out in the same manner as described in Example 1. The obtained results are shown in Table 4.

EXAMPLES 18 AND 19

A catalyst was prepared in the same manner as described in Example 17 except that strontium chloride or lanthanum chloride was used instead of potassium chloride, and by using 1.11 g of the thus-obtained catalyst, the chlorination reaction of MCB was carried out in the same manner as described in Example 1. The obtained results are shown in Table 4.

COMPARATIVE EXAMPLE 7

By using 1 g of K-L calcined at 540° C. for 3 hours under the circulation of air, the chlorination reaction of MCB was carried out in the same manner as described in Example 1. The obtained results are shown in Table 4.

COMPARATIVE EXAMPLES 8 AND 9

By using a catalyst of Sr-L or La-L type zeolite prepared by the same ion-exchange method as described in Comparative Example 2, the chlorination reaction of MCB was carried out in the same manner as described in Example 1. The obtained results are shown in Table 4.

COMPARATIVE EXAMPLE 10

A 2N aqueous solution of sodium chloride containing a sodium (Na) ion in an amount 20 times the amount of a potassium (K) ion contained in 10 g of K-L was prepared, and the solution was maintained at 90° C. by using a mantle heater. Then, 10 g of K-L was added to the solution, and the mixture was sufficiently stirred for 5 hours by a glass stirring vane. The obtained slurry was filtered and the solid was washed with 10 l of distilled water. This operation was repeated three times. The obtained solid was dried for 15 hours in a drier maintained at 130° C. and calcined at 540° C. for 3 hours under the circulation of air to obtain Na-L. The degree of Na ion exchange was 43%. By using 1 g of the thus-obtained catalyst, the chlorination reaction of MCB was carried out in the same manner as described in Example 1. The obtained results are shown in Table 4.

EXAMPLE 20

In a ceramic beaker having a capacity of 1 liter, 1.11 g of sodium chloride was dissolved in 150 ml of distilled water. The solution was maintained at 95° C. by using a warm bath, and 10 g of Na-L prepared in Comparative Example 10 was added to the solution with sufficient stirring by a glass stirring vane. Evaporation to dryness was conducted until water was completely removed. The solid was dried for 15 hours in a drier maintained at 130° C. and calcined at 540° C. for 3 hours under the circulation of air to obtain a catalyst of Na-L-10 wt. % NaCl. By using 1.11 g of the thus-obtained catalyst, the chlorination reaction of MCB was carried out in the same manner as described in Example 1. The obtained results are shown in Table 4.

TABLE 4

| | Catalyst | Conversion (%) of MCB | Selectivity (%) to PDCB |
|---|---|---|---|
| Comparative Example 7 | K—L | 62.6 | 87.7 |
| Example 17 | K—L—10 wt. % KCl | 60.5 | 91.5 |
| Comparative Example 8 | Sr—L | 67.8 | 87.2 |
| Example 18 | K—L—10 wt. % SrCl$_2$ | 72.3 | 88.1 |
| Comparative Example 9 | La—L | 68.3 | 84.5 |
| Example 19 | K—L—10 wt. % LaCl$_3$ | 66.2 | 87.6 |
| Comparative Example 10 | Na—L | 67.3 | 89.2 |
| Example 20 | Na—L—10 wt. % NaCl | 70.7 | 91.1 |

EXAMPLE 21

A catalyst was prepared in the same manner as described in Example 1 except that Na-X was used instead of Na-Y, and by using 1.482 g of this catalyst, the chlorination reaction of MCB was carried out in the same manner as described in Example 1. The obtained results are shown in Table 5.

EXAMPLE 22

A catalyst was prepared in the same manner as described in Example 17 except that Na-ZSM-5 was used instead of Na-Y, and by using 1.11 g of this catalyst, the chlorination reaction of MCB was carried out in the same manner as described in Example 1. The obtained results are shown in Table 5.

EXAMPLE 23

A catalyst was prepared in the same manner as described in Example 17 except that K-zeolite OE was used instead of K-L, and by using 1.11 g of this catalyst, the chlorination reaction of MCB was carried out in the same manner as described in Example 1. The obtained results are shown in Table 5. Note, the K-zeolite OE used in this Example is one of offretite/erionite type zeolite, and the synthesis process is disclosed in Japanese Unexamined Patent Publication No. 59-69,420.

COMPARATIVE EXAMPLE 11

By using 1 g of a catalyst of Na-X calcined at 540° C. for 3 hours under the circulation of air, the chlorination reaction of MCB was carried out in the same manner as described in Example 1. The obtained results are shown in Table 5.

COMPARATIVE EXAMPLE 12

By using 1 g of a catalyst of K-ZSM-5 prepared by the same ion-exchange method as described in Comparative Example 2, the chlorination reaction of MCB was carried out in the same manner as described in Example 1. The obtained results are shown in Table 5.

COMPARATIVE EXAMPLE 13

By using 1 g of a catalyst of K-zeolite OE calcined at 540° C. for 3 hours under the circulation of air, the chlorination reaction of MCB was carried out in the same manner as in Example 1. The obtained results are shown in Table 5.

TABLE 5

| Catalyst | | Conversion (%) of MCB | Selectivity (%) to PDCB |
|---|---|---|---|
| Comparative Example 11 | Na—X | 37.2 | 72.0 |
| Example 21 | Na—X-30 wt. % NaCl | 24.5 | 75.2 |
| Comparative Example 12 | K—ZSM-5 | 25.2 | 79.1 |
| Example 22 | Na—ZSM-5-10 wt. % KCl | 14.4 | 79.8 |
| Comparative Example 13 | K—zeolite OE | 36.9 | 78.0 |
| Example 23 | K—zeolite OE-10 wt. % KCl | 20.9 | 78.7 |

EXAMPLE 24

The chlorination reaction of toluene was carried out by using 1.428 g of the Na-Y-30 wt. % NaCl obtained in Example 1. The chlorination reaction of toluene was conducted in the same manner as described in Example 1 except that 30 g of toluene was used instead of MCB. The obtained results are shown in Table 6.

COMPARATIVE EXAMPLE 14

The chlorination reaction of toluene was carried out by using 1 g of Na-Y calcined at 540° C. for 3 hours under the circulation of air. The chlorination reaction of toluene was conducted in the same manner as described in Example 1 except that 30 g of toluene was used instead of MCB. The obtained results are shown in Table 6.

TABLE 6

| Catalyst | | Conversion (%) of Toluene | Selectivity (%) to p-Chlorotoluene |
|---|---|---|---|
| Comparative Example 14 | Na—Y | 68.4 | 56.5 |
| Example 24 | Na—Y—30 wt. % NaCl | 68.4 | 60.0 |

EXAMPLE 25

By using a ceramic mortar, 11 g of Na-Y (containing 10% by weight of adsorption water) was physically mixed with 4.29 g of sodium chloride, and the mixture was calcined at 540° C. for 3 hours under the circulation of air to obtain Na-Y-30 wt. % NaCl. By using 1.428 g of the so-obtained catalyst, the chlorination reaction of MCB was carried out in the same manner as described in Example 1. It was found that the conversion of MCB was 68.2% and the selectivity to PDCB was 82.1%. Note, the amount of adsorption water contained in the zeolite is a value calculated from the weight loss by removal of water by a thermobalance when the temperature is elevated from room temperature to 500° C.

We claim:

1. A process for the preparation of p-dichlorobenzene, a p-chlorinated monohalogenated benzene or a p-chlorinated monoalkyl benzene having 1 to 10 carbon atoms in the alkyl group, from benzene, a monohalogenated benzene or a monoalkyl benzene having 1 to 10 carbon atoms in the alkyl group, respectively, which comprises chlorinating benzene, a monohalogenated benzene or a monoalkyl benzene having 1 to 10 carbon atoms in the alkyl group in the liquid phase at a temperature of 0° to 400° C. by using chlorine as a chlorinating agent, wherein a zeolite placed in intimate contact with a metal salt selected from the group consisting of halide, nitrate, carbonate or sulfate of an alkali metal, an alkaline earth metal or lanthanum is used as a catalyst for the chlorination.

2. A process according to claim 1, wherein the zeolite is selected from the group consisting of zeolite Y, zeolite L, zeolite X, gmelinite, zeolite ZSM-5, offretite/erionite type zeolite and mordenite.

3. A process according to claim 1, wherein the zeolite is selected from the group consisting of zeolite Y and zeolite L.

4. A process according to claim 1, wherein the metal salt is a chloride, nitrate, carbonate or sulfate of sodium, potassium, rubidium, cesium, magnesium, calcium, strontium, barium or lanthanum.

5. A process according to claim 1, wherein the amount of the metal salt is in the range of 0.1 to 90% by weight based on the weight of the catalyst.

6. A process according to claim 1, wherein the amount of the metal salt is in the range of 10 to 80% by weight based on the weight of the catalyst.

7. A process according to claim 6, wherein the zeolite placed in intimate contact with the metal salt is prepared by conducting at least once the steps of impregnating the zeolite with a solution of the metal salt in a solvent and then drying the metal salt solution-impregnated zeolite at a temperature of 80° to 150° C.

8. A process according to claim 7, wherein the dried zeolite is calcined at a temperature of 200° to 900° C. in an air or inert gas atmosphere.

9. A process according to claim 1, wherein the zeolite placed in intimate contact with the metal salt is prepared by mixing the zeolite with the metal salt in the state where the zeolite contains at least 0.1% by weight of water, and then drying the metal salt-mixed zeolite.

10. A process according to claim 9, wherein the dried zeolite is calcined at a temperature of 200° to 900° C. in an air or inert gas atmosphere.

11. A process according to claim 1, wherein the chlorination is carried out in the liquid phase at a temperature of 20° to 150° C.

12. A process according to claim 1, wherein the chlorination is carried out in a continuous manner is which 0.01 to 5 moles of gaseous chlorine as a chlorinating agent per mole of the aromatic hydrocarbon is introduced into a reaction liquid.

* * * * *